United States Patent [19]

Staff

[11] 4,194,400
[45] Mar. 25, 1980

[54] ULTRASONIC INSPECTION METHOD

[75] Inventor: Bonner W. Staff, Cincinnati, Ohio

[73] Assignee: General Electric Company, Cincinnati, Ohio

[21] Appl. No.: 862,791

[22] Filed: Dec. 21, 1977

[51] Int. Cl.² ............................................. G01N 29/04
[52] U.S. Cl. ..................................................... 73/623
[58] Field of Search ........................... 73/622, 623, 629

[56] References Cited

U.S. PATENT DOCUMENTS

| | | | |
|---|---|---|---|
| 2,527,986 | 10/1950 | Carlin | 73/629 |
| 3,485,088 | 12/1969 | O'Connor | 73/629 |
| 3,678,736 | 7/1972 | May | 73/634 |
| 3,739,262 | 6/1973 | Seekins | 324/234 |
| 3,778,170 | 12/1973 | Howell et al. | 356/241 |
| 3,826,127 | 7/1974 | Molina | 73/629 |
| 3,929,005 | 12/1975 | Parkinson et al. | 73/622 |
| 4,030,344 | 6/1977 | Northeved et al. | 73/629 |
| 4,041,774 | 8/1977 | Morris et al. | 73/629 |

Primary Examiner—Anthony V. Ciarlante
Attorney, Agent, or Firm—Lee H. Sachs; Derek P. Lawrence

[57] ABSTRACT

The inspection of a portion of an internal member of an assembled article, unavailable for direct line inspection, for example portions of the rotor of a gas turbine engine, is accomplished through the use of an ultrasonic probe inserted through an access port of the article toward a surface of the member to be inspected. As a result of predetermined positioning of a transducer in the operating head of the probe to bounce an ultrasonic signal from an internal boundary toward the portion to be inspected and the comparison between predetermined and received signals, along with an analysis of the comparison, determines whether a defect is present in the member.

3 Claims, 7 Drawing Figures

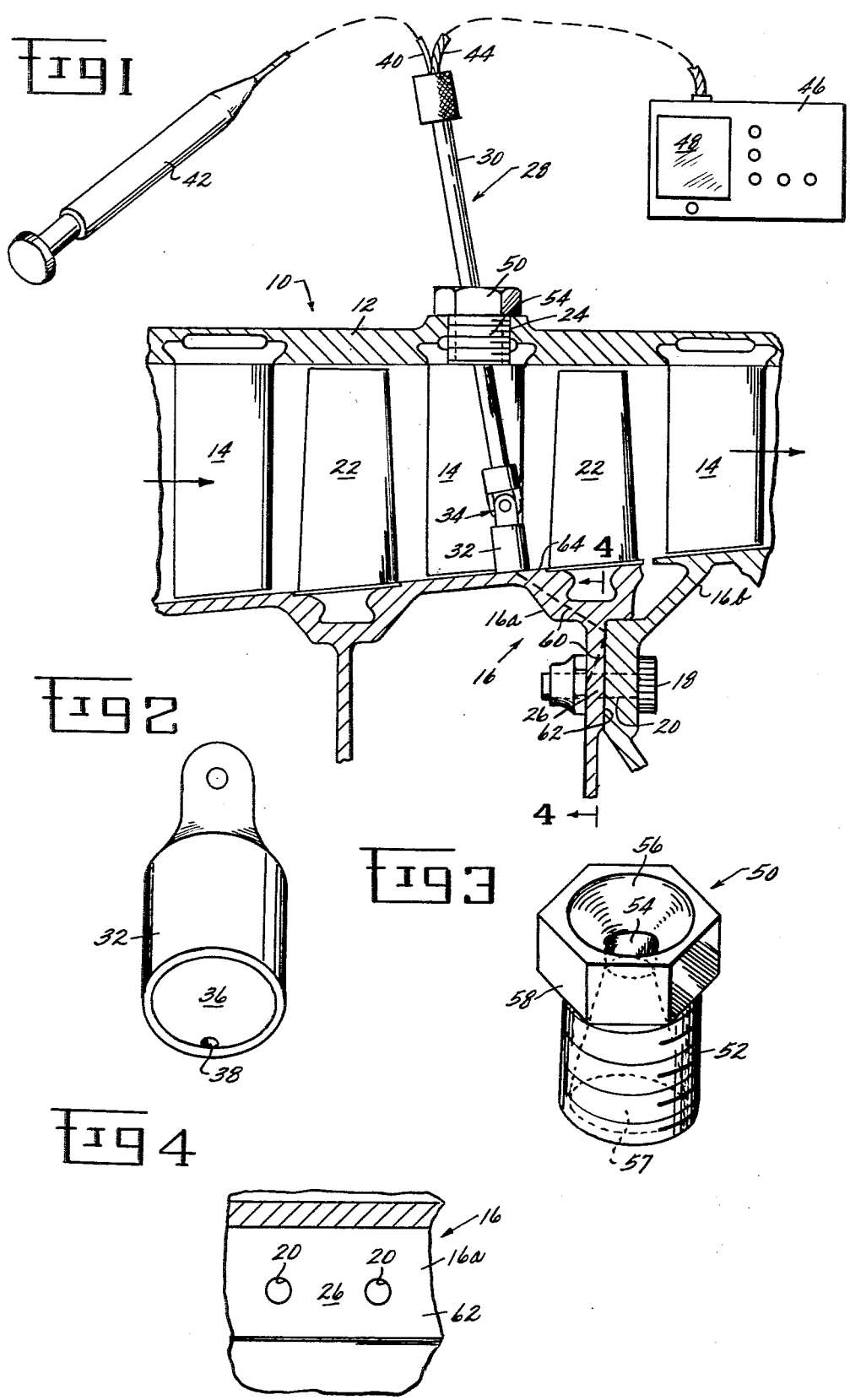

ULTRASONIC INSPECTION METHOD

BACKGROUND OF THE INVENTION

This invention relates to ultrasonic inspection of articles and, more particularly, to the improved blind inspection of a member within an assembled article through an access port, for example the inspection of a gas turbine engine rotor through a borescope opening while the rotor is assembled in the engine.

The primary power source for present aircraft is the gas turbine engine. Also, a variety of land-based or marine applications of such power producing apparatus has been developed. Among the technology advances in such an art has been the significant increase in safe operating life of individual members or components assembled into such an engine. Nevertheless, earlier inspection of such members sometimes becomes desirable and informative.

In order to provide limited observation of components within a gas turbine engine while the engine is still assembled, access ports have been designed in the walls of members, such as casings, to provide for the borescopic, optical inspection of internal members. One such inspection device and method is shown in U.S. Pat. No. 3,778,170—Howell et al, issued Dec. 11, 1973, the disclosure of which is incorporated herein by reference.

The ultrasonic inspection technique, to which the present invention more particularly relates, is a well known and highly developed art. In general, it involves sending an electrical impulse to a transducer which converts the impulse into ultrasonic frequency mechanical vibrations and transmits such vibrations through a liquid couplant such as water, glycerine or an oil, to an article. Such a signal will be reflected by any surface it encounters on or in the article. Electrical analysis apparatus or instruments are commercially available to assist in the identification of any reflected signal for the determination of defects, including flaws and discontinuities, within the article member being inspected. As used in this specification, the term "defects" is intended to include any such condition predetermined to be undesirable within an article. As a nondestructive testing or inspection means, ultrasonic techniques have been found to be useful in determining the quality of a variety of articles in which internal defects can occur during their manufacture.

During use of ultrasonic inspection, it is required that the transducer be properly positioned with respect to the surface of a member which is being inspected. Therefore, the use of such an inspection technique within an assembled article, for the fluid inspection of a member portion difficult to reach by normal methods, has presented difficult positioning and alignment problems. In addition, the inaccessibility of portions of a member to be inspected has precluded the direct transmission of an ultrasonic signal toward the protion.

SUMMARY OF THE INVENTION

It is a principal object of the present invention to provide an improved ultrasonic method for the blind inspection of an internal portion of a member within an assembled article.

This and other objects and advantages will be more clearly understood from the following detailed description, the examples, and the drawing, all of which are intended to be typical of rather than in any way limiting on the scope of the present invention. Briefly, one form of the present invention for the ultrasonic examination for defects in a portion of a member not directly accessible to straight line ultrasonic vibration signal includes providing a predetermined normal signal form associated with the member portion to be examined. Then an ultrasonic signal is directed within the member toward at least one bondary of the member from which it is deflected toward the member portion. Such signal is reflected from such portion and received outside of the member. Thereafter, the received signal and the predetermined normal signal are compared to determine or examine for the presence of a defect in the member portion so inspected.

One form of the apparatus associated with the present invention is an ultrasonic probe assembly which includes an operating head connected to a probe body through a mechanical coupling, such as a universal joint, allowing multidimensional movement of the head with respect to the body. The operating head carries a transducer having a transducer face intended to cooperate with a surface of a member to be examined. The probe body carries, in sliding relationship, guide means adapted to be secured to an access port in the article to assist in positioning and guiding the operating head within the article at the member surface and in providing for angular movement and rotation of the probe in respect to such surface as well as sliding of the probe toward and away from such member surface. In addition, included is means to dispose the liquid couplant, preferably at the transducer face, between the transducer face and the member surface.

DESCRIPTION OF THE DRAWINGS

Although the specification concludes with claims particularly pointing out and distinctly claiming the subject matter of this invention, it is believed that the invention will be better understood upon reading the following detailed description of the preferred embodiments taken in connection with the accompanying drawings. It is not intended by such description and drawings to limit the scope of the appended claims. In the drawings:

FIG. 1 is a fragmentary, partially sectional, partially diagrammatic view of a portion of an axial flow gas turbine engine compressor with apparatus in position to practice the method associated with the present invention;

FIG. 2 is an enlarged, perspective view of the ultrasonic probe operating head shown in FIG. 1;

FIG. 3 is an enlarged perspective view of a guide means adapted to be secured to the assembly in FIG. 1 and to allow sliding and angular movement of the probe as shown in FIG. 1;

FIG. 4 is a fragmentary view of a portion of a compressor member and bolt hole in FIG. 1, taken along line 4—4.

DESCRIPTION OF THE PREFERRED EMBODIMENTS

Figure 5:
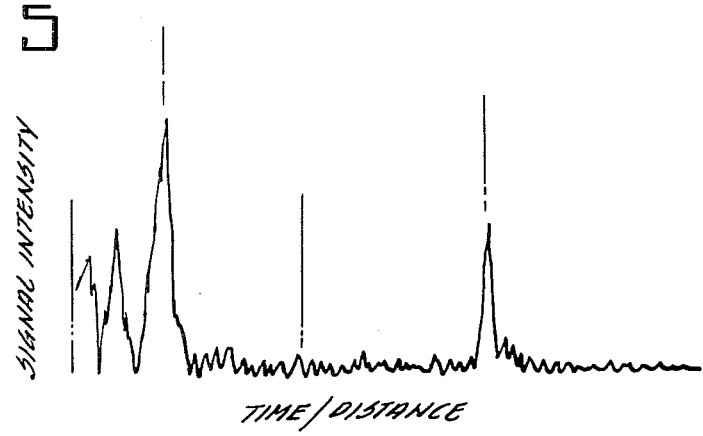
FIGS. 5, 6 and 7 are graphical presentations of signals reflected and analyzed in the practice of the present invention.

The present invention is particularly useful in connection with the ultrasonic examination of an internal component of a gas turbine engine, for example of the type identified in the above-incorporated U.S. PAT. No. 3,778,170. Thus, it can be used in the examination in that type of gas turbine engine a portion of which is shown in partial section in FIG. 1. In that figure, the compressor, shown generally at 10, includes an outer stationary wall 12 which carries compressor stator vanes 14. Spaced within the outer wall 12 is an inner member or compressor rotor drum or discs shown generally at 16 comprised of a plurality of cooperating members such as 16a and 16b held together by a coupling means such as bolts 18 disposed through bolt holes 20 shown in phantom in FIG. 1 and in more detail in FIG. 4. For example, if 16a and 16b represent drum-like discs, then a plurality of bolts and associated bolt holes would be disposed circumferentially about the member as shown in FIG. 4. A plurality of rotating blading members 22 is carried by member 16. Disposed through outer wall 24 is at least one borescope opening of the type described in the above-incorporated U.S. Pat. No. 3,778,170 to provide visual access within the compressor.

After a period of operation of a gas turbine engine, it may become disirable to determine the presence of any defects, such as discontinuities or cracks, in member 16a in the vicinity of bolt holes 20, for example in the portion between such bolt holes identified as 26 in FIG. 4. Prior to the present invention, for an accurate determination of any such defects, discontinuities or cracks, it was necessary to disassemble the inner member or rotor 16 from within outer wall or casing 12 and then to separate members such as 16a and 16b through the removal of bolts 18 from bolt holes 20. Through the present invention, portion 26 of member 16a can be examined ultrasonically without such disassembly and while the engine not only is fully assembled but also while the engine is mounted in apparatus such as an aircraft.

As can be seen from FIG. 1, the portion 26 between bolt holes 20 in member 16a is inaccessible to direct line ultrasonic inspection in the normal fashion. Accordingly, the present invention provides novel apparatus and an associated method for the indirect ultrasonic examination of such portion. An ultrasonic probe shown generally at 28 includes a probe body 30 and an operating head 32 connected to the probe body through a mechanical coupling 34 shown in FIG. 1 to be a typical universal joint. Such coupling or joint allows multidimensional movement of the operating head with respect to the body. Operating head 32, shown in more detail in FIG. 2, carries a transducer having a transducer face 36 through which is provided an opening 38 for the disposition of a liquid couplant such as water, glycerine or a light oil. Opening 38 is connected to flexible conduit or tubing 40 in FIG. 1 through which liquid couplant is passed, for example as a result of the operation of a syringe 42 or other pumping means.

The transducer, represented by transducer face 36, is electrically connected through conductor 44 to a means for the generation, transmission and evaluation of ultrasonic signals, presented in FIG. 1 as instrument 46, for example including an oscilloscope 48 for the visual presentation of the form of reflected ultrasonic signals. Such apparatus and its association with ultrasonic probes which include transducers are commercially available and are well known in the art, for example as described in U.S. Pat. No. 3,147,613, issued Sept. 8, 1964, the disclosure of which is incorporated herein by reference.

Also associated with ultrasonic probe 28 is a guide means such as threaded member or nut 50, shown in more detail in FIG. 3 and adapted to be secured such as through threads 52 to threaded borescope opening 24. With reference to FIG. 3, one portion of member 50 includes therethrough a channel 54 sized to be larger than the cross section of probe body 30 to allow body 30 to slip freely through channel 54. Such portion of member 50 also includes a relief portion or conical indentation 56 through head 58 and the opposite portion includes enlarged opening 57 to allow angular movement and axial rotation of the probe as well as sliding of the probe through member 50 for example toward and away from member 16.

Figure 7:
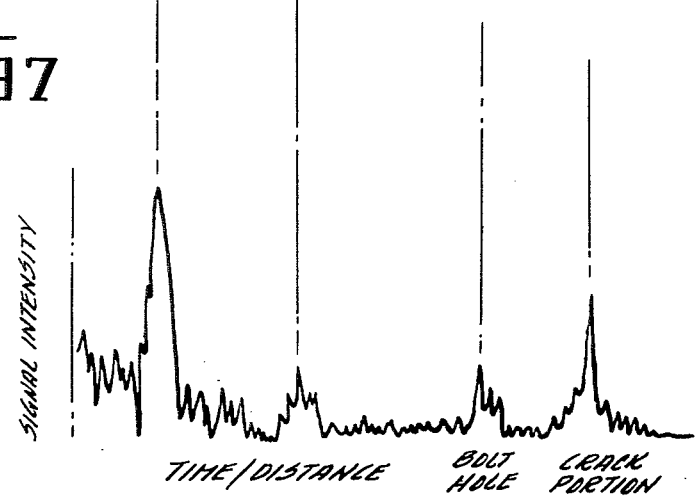

In the practice of the method associated with the present invention, a preliminary calibration and signal form determination is made for the particular portion of the member being inspected in order to establish a standard or predetermined normal for comparison. Such a signal form of the type shown in FIG. 5 is produced under controlled conditions, for example in a laboratory on a sample representative of or simulating the member being inspected. With reference to the member 16a in FIG. 1, it can be seen that there is no straight line ultrasonic path to member portion 26 in the vicinity of bolt holes 20. Therefore, an indirect path, represented by broken line 60 in FIG. 1, must be used for the ultrasonic vibration or signal path. According to the present invention, an ultrasonic signal is projected along such a path as broken line 60 toward the interface or boundary 62 between members 16a and 16b, from which such signal is deflected toward portion 26 of member 16a when the angular disposition and location of transducer face 36 is properly adjusted on surface 64 of member 16a. Thus, the predetermination of the normal signal for the particular member being examined provides a basis for later comparison during practice of the invention on an assembled article, with the member being accessible only remotely through a port such as borescope opening 24. The result of such a predetermination is the type of signal form shown in FIG. 5, clearly pointing out the time/distance position of the various reflections along path 60, including the position of bolt hole 20. Other predetermined normal signal standards, not shown, can be generated to include specific defects, such as cracks, if specimens or simulations of such defects are available. In such a case, for example in connection with FIG. 5, the signal form would include a peak of greater signal intensity than the background at a point beyond the time/distance point of the bolt hole peak shown in FIG. 5, similar to that shown in FIG. 7 for an actual, assembled inspection.

Figure 6:
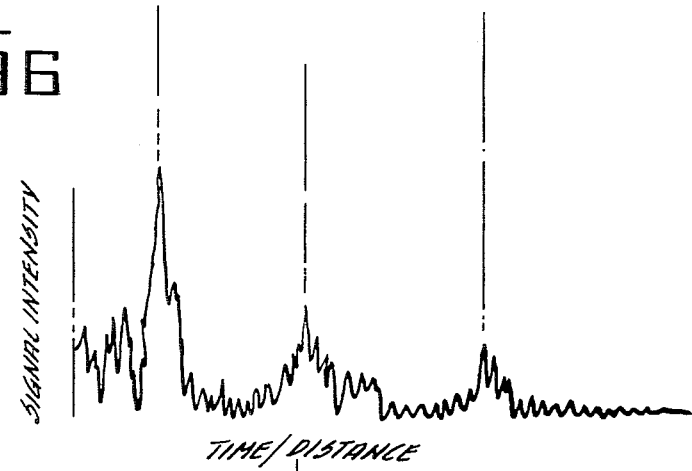

With the establishment of such standard as a basis for later comparison, practice of the present invention on an assembled article such as that shown in FIG. 1 includes inserting into an access port such as borescope opening 24 in FIG. 1, operating head 32, mechanical coupling means 34 and a protion of body 30 of probe 28 so that operating head 32 approaches surface 64 of member 16a. Guide member 50 is secured to outer wall 12 thus maintaining operating head 32 and coupling 34 generally within the interior of compressor 10. When operating head 32 is positioned in respect to member 16a so that transducer face 36 is in general operating relationship with surface 64, pumping means such as syringe 42 is activated to dispose a liquid couplant, of a type commonly used in ultrasonic examination, through opening 38 and between surface 64 and transducer face 36. Instrument 46 is activated to transmit preliminary electric impulses to the transducer which converts the impulses into ultrasonic frequency mechanical vibrations. Such vibrations then are transmitted by the transducer through the transducer face 36 and the liquid couplant as a preliminary signal to member 16a through surface 64. In the embodiment shown in FIG. 1, oscilloscope 48 is observed to determine the form of ultrasonic signal reflected from member 16a through the transducer to instrument 46. If the reflected signal substantially does not match the predetermined normal signal for the configuration of member 16a, then the transducer face is moved along surface 64, through any necessary angular or rotational movement of probe body 30 and coupling 34, until the reflected signal from such preliminary transmitted signal substantially matches the predetermined normal signal. In that position, a first transmitted ultrasonic signal would follow a path such as broken line 60 toward portion 26 between bolt holes 20, the signal having been deflected internally from boundary 62. Because, in this example, it is desirable to examine an area adjacent bolt hole 20, a second or reflected signal similar to that shown in FIG. 6 will be obtained for the configuration of member 16a, the signal intensity of the bolt hole being somewhat less than that which would be achieved if the vibrations were directed solely to maximize the bolt hole portion of the reflected signal. The configuration of FIG. 6 is that which exists when no defect such as a crack is present. However, if there is a crack in the vicinity of the bolt hole, the reflected signal will be that of the type shown in FIG. 7, clearly showing the cracked portion in the area of the bolt hole. The operator can rotate and move transducer face 36 with the object of obtaining a maximum signal intensity for such defects as a crack. Thus, an operator of the apparatus associated with the present invention can, by moving probe 28 in various positions along surface 64, determine through a comparison between a predetermined normal signal and a reflected ultrasonic signal observed through instrument 46 whether or not an internal defect, such as a crack, exists in a member portion being examined.

Although this embodiment employs a visual presentation of the ultrasonic signal reflected from the portion being examined, it will be understood that a variety of means can be used for the comparison and the signal matching, or lack of matching, and the existence of defects determined by the ultrasonic signal. For example, a program representing a predetermined normal signal can be introduced into a computer which will compare the reflected signals with the predetermined normal signal and report the character of the comparison.

Thus, the present invention provides the capability for the ultrasonic examination for defects in a portion of a member while the member is assembled within an article and has limited accessibility outside the assembled article. Although the invention has been described in connection with specific embodiments, it will be understood by those skilled in the art, the variations and modifications of which the invention is capable within the scope of the appended claims.

What is claimed is:

1. In a method for the ultrasonic examination for a defect in the vicinity of a hole in a portion of a member while the member is assembled in an article which includes an outer wall having an access port available to a surface of the member, the member portion being inaccessible to straight line ultrasonic signals within the member from said member surface, the steps of:

providing a predetermined normal ultrasonic signal form associated with the member portion and the hole;

placing a face of an ultrasonic transducer through the access port and into operating position at the member surface;

activating the transducer to direct a first ultrasonic signal within the member through the member surface and toward at least one boundary of the member remote from the member portion, the signal being directed along a path within the member in respect to the boundary and the member portion such that the first signal is deflected from the boundary toward the member portion;

receiving from the member portion, through the transducer, a second ultrasonic signal which is a reflection of the first signal; and then, comparing the form of the second signal with the predetermined normal signal form to examine for the presence of a defect in the member portion.

2. The method of claim 1 in which the step of placing a face of an ultrasonic transducer into operating position at the member surface comprises the steps of:

first placing the transducer at the member surface;

directing the first signal generally toward the member portion as a preliminary first signal and receiving a reflected signal of the preliminary signal from the member portion;

determining whether the preliminary signal is directed to the member portion by comparing the form of the reflected signal with the predetermined normal signal form; and then, if the forms of the reflected and predetermined normal signals are substantially different thereby indicating misdirection of the preliminary first signal, moving the transducer face along the member surface until the reflected and predetermined normal signal forms are substantially the same.

3. The method of claim 1 for the ultrasonic examination for defects in a portion of a turbine engine member assembled within and spaced apart from an outer casing of the engine, the casing having an access port therethrough available to a surface of the member, including the additional steps, prior to activating the transducer, of:

providing an ultrasonic probe including an operating head carrying a transducer having a transducer face; and then inserting the operating head through the access port toward the member surface to place the transducer face into operating position at the member surface.

* * * * *